United States Patent
Marlot et al.

(10) Patent No.: US 12,154,324 B1
(45) Date of Patent: Nov. 26, 2024

(54) AUTOMATED IMAGE-BASED ROCK TYPE IDENTIFICATION WITH NEURAL-NETWORK SEGMENTATION AND CONTINUOUS LEARNING

(71) Applicant: Schlumberger Technology Corporation, Sugar Land, TX (US)

(72) Inventors: Maxime Marlot, Kuala Lumpur (MY); Matthias Francois, Clamart (FR)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 0 days.

(21) Appl. No.: 18/720,042

(22) PCT Filed: May 31, 2023

(86) PCT No.: PCT/US2023/023919
§ 371 (c)(1),
(2) Date: Jun. 14, 2024

(87) PCT Pub. No.: WO2023/235347
PCT Pub. Date: Dec. 7, 2023

(30) Foreign Application Priority Data

May 31, 2022 (EP) .................................. 22305794

(51) Int. Cl.
*G06V 10/98* (2022.01)
*G06V 10/26* (2022.01)
(Continued)

(52) U.S. Cl.
CPC ............ *G06V 10/993* (2022.01); *G06V 10/26* (2022.01); *G06V 10/771* (2022.01); *G06V 10/82* (2022.01); *G06V 20/10* (2022.01)

(58) Field of Classification Search
CPC .... G06V 10/993; G06V 10/771; G06V 10/82; G06V 20/10; G06V 10/26
See application file for complete search history.

(56) References Cited

U.S. PATENT DOCUMENTS 11,788,408 B2 * 10/2023 Ismailova ............ G01N 33/241
73/152.11
2019/0338637 A1 11/2019 Francois et al.
(Continued)

FOREIGN PATENT DOCUMENTS

WO 2022032057 A1 2/2022

OTHER PUBLICATIONS

Becerra, Daniela, et al. "Generating a labeled data set to train machine learning algorithms for lithologic classification of drill cuttings ." Interpretation 10.3 (2022): SE85-SE100. (Year: 2022).*
(Continued)

*Primary Examiner* — Utpal D Shah
(74) *Attorney, Agent, or Firm* — Jeffrey D. Frantz

(57) ABSTRACT

A method for evaluating drill cuttings includes acquiring a first digital image and processing the first digital image with a trained neural network (NN) to generate a first segmented image including a plurality of labeled segments in which at least one label includes a lithology type. The segmented image and the acquired first digital image are processed to retrain the NN. A second digital image is then be processed with the retrained NN to generate a second segmented image including a plurality of labeled segments in which at least one label includes a lithology type.

18 Claims, 6 Drawing Sheets

(51) Int. Cl.
   *G06V 10/771* (2022.01)
   *G06V 10/82* (2022.01)
   *G06V 20/10* (2022.01)

(56) References Cited

U.S. PATENT DOCUMENTS

| | | | |
|---|---|---|---|
| 2020/0340907 A1 | 10/2020 | Allo | |
| 2021/0133474 A1* | 5/2021 | Sawada | G06N 3/045 |
| 2021/0319257 A1 | 10/2021 | Francois et al. | |
| 2022/0018241 A1 | 1/2022 | Affleck | |
| 2022/0327713 A1* | 10/2022 | Maximo | G06N 3/045 |
| 2023/0220761 A1* | 7/2023 | Yamada | G06T 7/74 |
| | | | 175/24 |
| 2023/0374903 A1* | 11/2023 | Al-Qubaisi | E21B 49/005 |
| 2024/0054766 A1* | 2/2024 | Yu | G06V 10/14 |

OTHER PUBLICATIONS

Search Report and Written Opinion of International Patent Application No. PCT/US2023/023919 dated Sep. 21, 2023, 9 pages.

Kathrada, M. et al., "Visual Recognition of Drill Cuttings Lithologies Using Convolutional Neural Networks to Aid Reservoir Characterisation", SPE-196675-MS, presented at the SPE Reservoir Characterisation and Stimulation Conference and Exhibition, Abu Dhabi, UAE, 2019.

YouTube Video "15FORCE Wade Deep Learning on Cuttings Images—Computer Vision for Geoscience Interpretation" 2019, https://www.youtube.com/watch?v=Wh6PO9qxA5l.

* cited by examiner

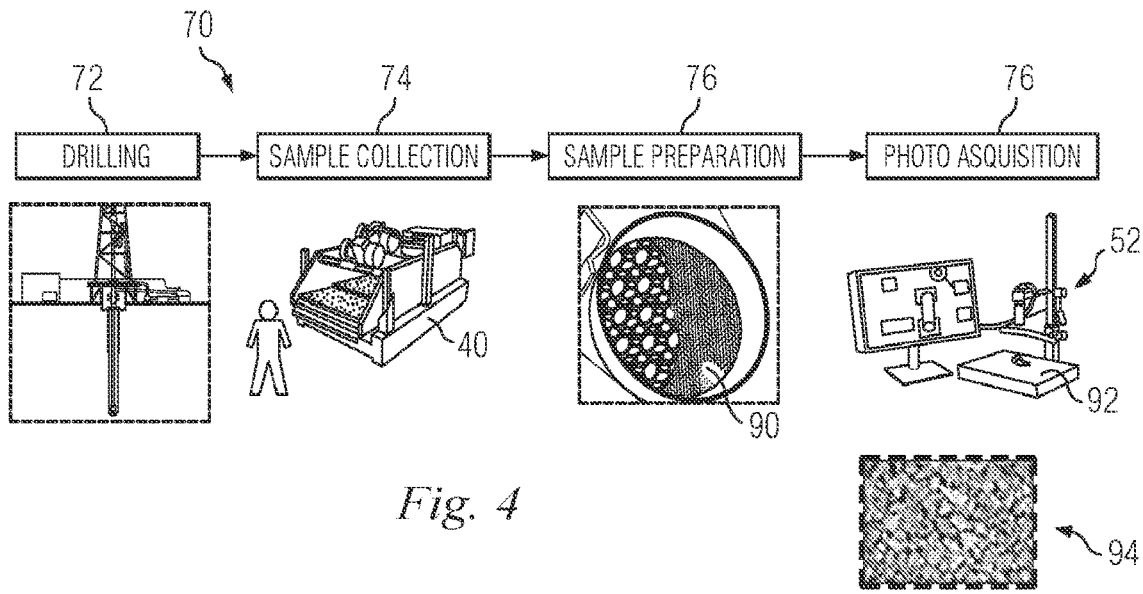
Fig. 4
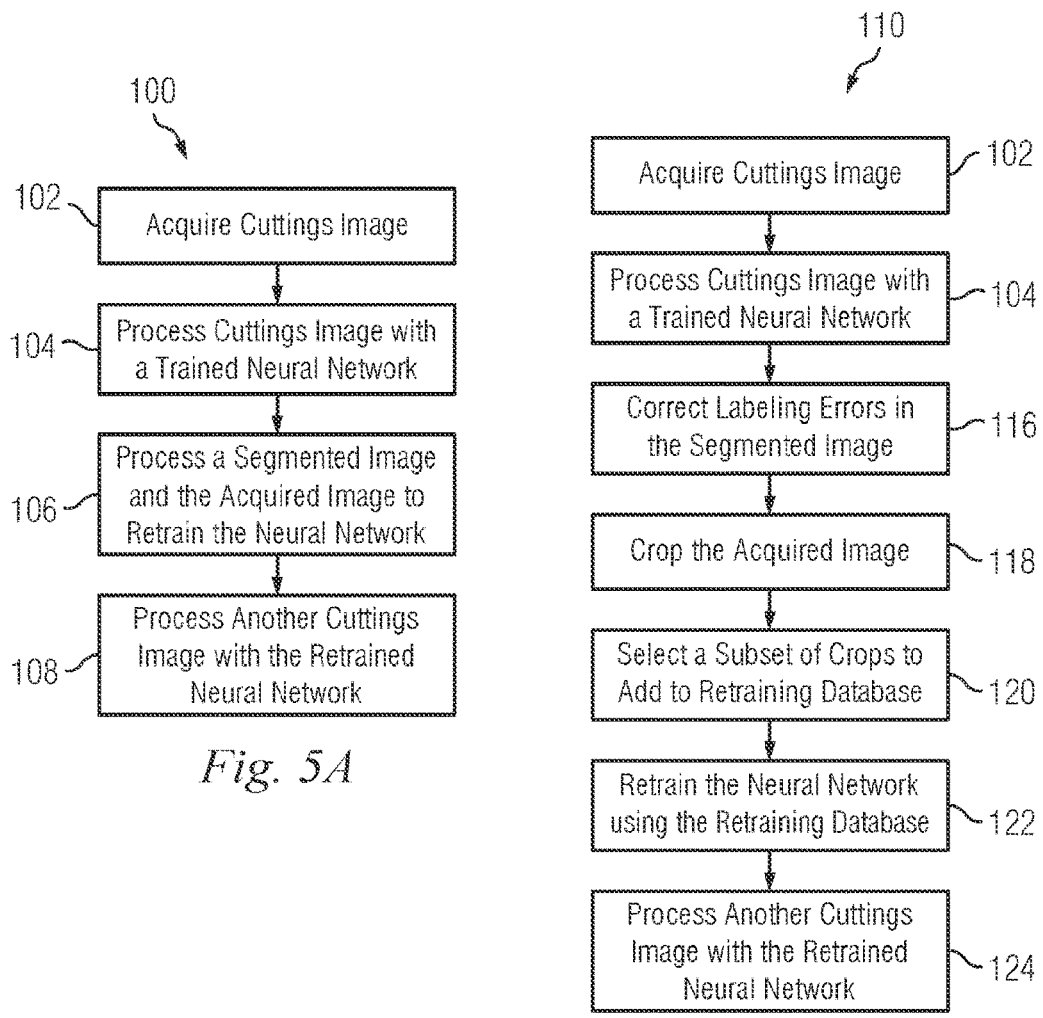
Fig. 5A
Fig. 5B

Cropped Image

Selected Subset of Crops

Smart Crop Selection Algorithm

Add Selected Crops to Retraining Database

Sandstone

Shale

Updated Retraining Database

Retrain Selected Layers of NN

Process Next Image Using Retrained NN

AUTOMATED IMAGE-BASED ROCK TYPE IDENTIFICATION WITH NEURAL-NETWORK SEGMENTATION AND CONTINUOUS LEARNING

CROSS REFERENCE TO RELATED APPLICATIONS

This application is the National Stage Entry of International Application No. PCT/US2023/023919, filed May 31, 2023, which claims priority to European Patent Application No. 22305794.4, which was filed on May 31, 2022, and each of the above applications is incorporated herein by reference in its entirety.

BACKGROUND

In subterranean drilling operations, such as for oil and gas exploration and production, formation cuttings are generated by the drilling activity. These cuttings have long been evaluated and characterized to better understand the properties and structure of subsurface rock. The cuttings are commonly collected after passing the shale shakers, then cleaned and photographed for analysis. In recent years there has been a desire to perform such evaluation and characterization automatically (or semi-automatically) to reduce human cost and shorten the turnaround time of the interpretation. However, implementing such automation is far from routine.

Electronic image data is commonly evaluated manually during conventional drilling operations. Automatic evaluation and characterization of such data is particularly challenging since the cuttings include a wide variety of sizes, shapes, textures, and colors. Moreover, the cuttings are commonly jumbled together in the image with individual particles touching and partially overlapping one another. Image lighting also tends to vary from image to image and rig to rig with shadowing and other image artifacts making the evaluation and characterization more challenging.

While machine learning algorithms have been disclosed for evaluating rock cuttings images, they generally require large computational times and are often not sufficiently accurate for reliable deployment. There is a need in the industry for improved methods for automatic image evaluation to improve timeliness and accuracy of the evaluation.

BRIEF DESCRIPTION OF THE DRAWINGS

For a more complete understanding of the disclosed subject matter, and advantages thereof, reference is now made to the following descriptions taken in conjunction with the accompanying drawings, in which:

FIG. 4 depicts an example process for obtaining cuttings images.

FIGS. 5A and 5B (collectively FIG. 5) depict flow charts of example methods for segmenting a digital image to identify and label one or more lithology types in the image.

DETAILED DESCRIPTION

Figure 1:
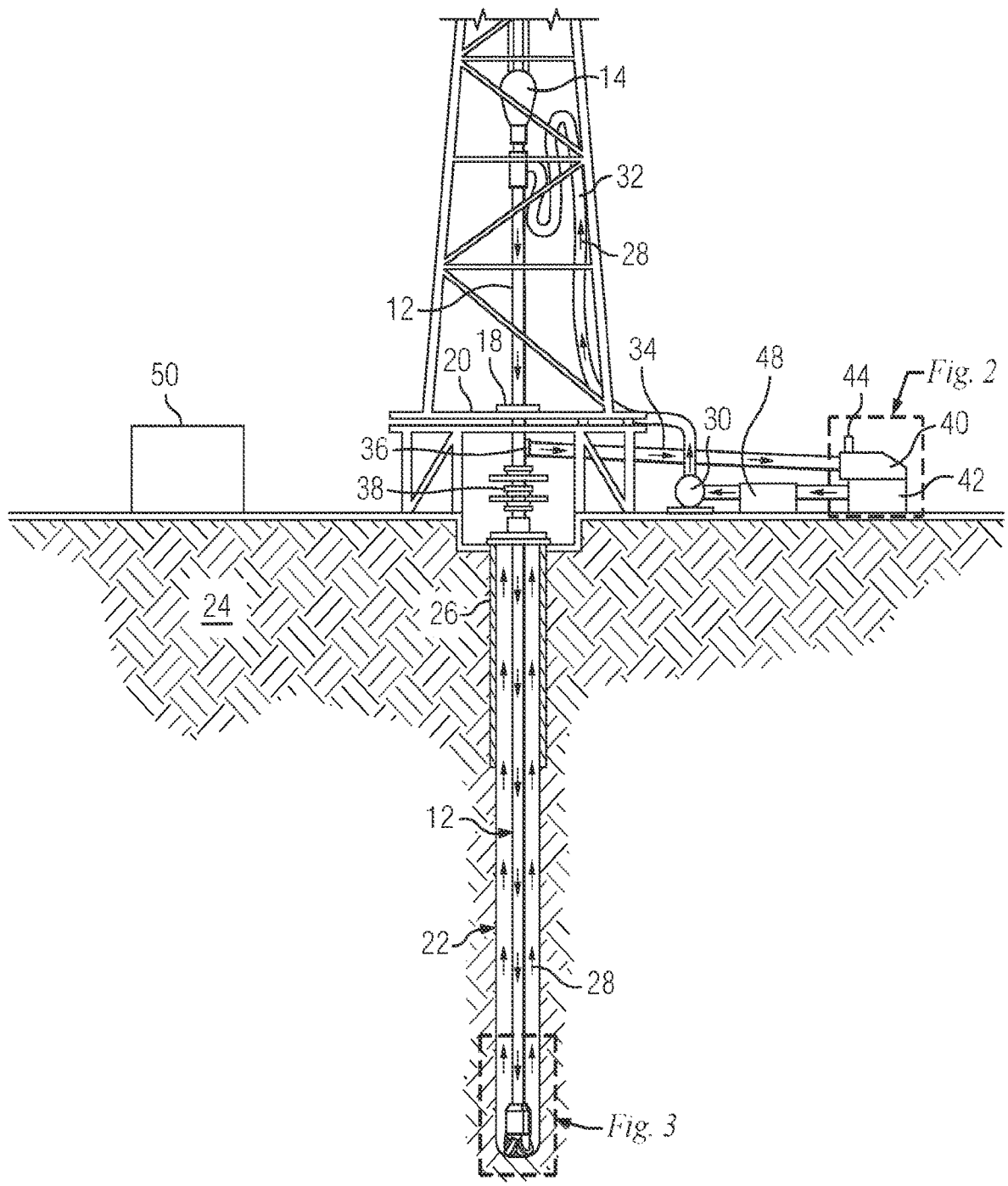
FIG. 1 depicts an example drilling rig including a system for automatically evaluating cuttings images.

Improved methods are disclosed for segmenting a digital image to identify and label one or more lithology types in the image during a wellbore drilling operation. The disclosed methods may advantageously improve the accuracy and timeliness of the image evaluation. In one example embodiment, a disclosed method may include acquiring a first digital image and processing the first digital image with a trained neural network (NN) to generate a first segmented image including a plurality of labeled segments in which at least one label includes a lithology type. The segmented image and the acquired first digital image may be processed to retrain the NN. A second digital image may then be processed with the retrained NN to generate a second segmented image including a plurality of labeled segments in which at least one label includes a lithology type.

As known to those of ordinary skill, drilling a subterranean borehole (e.g., in oil and gas exploration and/or production operations) generates a large volume of rock cuttings that are available at the rig site. In current drilling operations these cuttings are commonly evaluated by geologists, petrophysicists, and/or other experts at the rig site, for example, to evaluate local lithology and the oil bearing potential of the well. The cuttings description and evaluation is generally a manual and repetitive task performed at the rig site. A commonly implemented workflow involves rig personnel identifying each lithology type by visually examining the cuttings and performing chemical and/or physical measurements on cuttings samples. Upon identifying the lithology types in the cuttings sample, the operator describes the rock characteristics (color, hardness, grain size, etc.), for example, on paper. Photograph of the cuttings sample (digital images) may also be visually evaluated based on prior measurements and experience.

With the rise of image datasets in recent years, as well as advances in machine learning (ML), attempts have been made to automatically perform cuttings identification utilizing ML algorithms. Such attempts have included performing classification of cuttings from photographic images of drilling cuttings (e.g., using deep convolutional neural network analysis). Convolutional neural networks (CNN) have been trained to perform cuttings segmentation to classify each pixel, rock, or segment in a cuttings image. CNN models have been trained on datasets of cutting sample images collected from lithologies around the world and manually annotated at both the pixel-level (assigning a label to each image pixel) and at a rock or segment level (assigning a label to each rock or segment in the image). While such efforts have been extensive, they have had only limited success. One particular difficulty has been accurately labeling multiple rock types within a single image, such as may appear during a transition from one lithology to another during a drilling operation. A related difficulty has been accurately identifying a change from one lithology type to another in successive images (as can also happen when transitioning from one lithology type to another during drilling).

FIG. 1 depicts an example drilling rig 10 including a system 50 configured to automatically evaluate cuttings images. In the depicted embodiment, a drill string 12 may be suspended at an upper end by a kelly 12 and a traveling block 14 and terminate at a lower end at a drill bit 16. The drill string 12 and the drill bit 16 may be rotated, for example, by a rotary table 18 on a driller floor 20, thereby drilling a borehole (wellbore) 22 into an earth formation 24, where a portion of the borehole 22 may be cased by a casing 26. As illustrated, in certain embodiments, drilling fluid or drilling "mud" 28 may be pumped by a mud pump 30 into the upper end of the hollow drill string 12 through a connecting mud line 32. From there, the drilling fluid 28 may flow downward through the drill string 12, exiting the drill string 12 through openings in the drill bit 16, and may return to the surface by way of an annulus formed between the wall of the borehole 22 and an outer diameter of the drill string 12. Once at the surface, the drilling fluid 28 may return through a return flow line 34, for example, via a bell nipple 36. As illustrated, in certain embodiments, a blowout preventer 38 may be used to prevent blowouts from occurring in the drilling operation 10.

Figure 2:
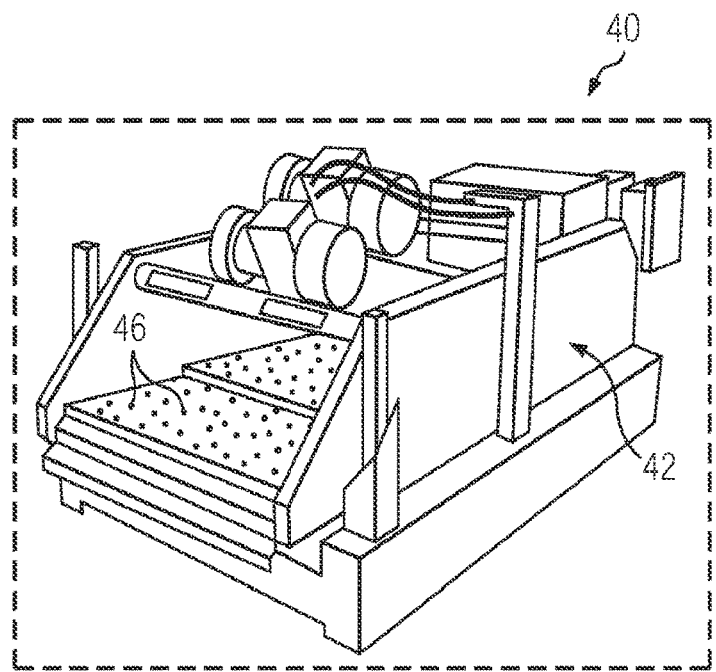
FIG. 2 depicts an example apparatus configured to remove drill bit cuttings from the drilling fluid in use in the rig depicted on FIG. 1.
Figure 3:
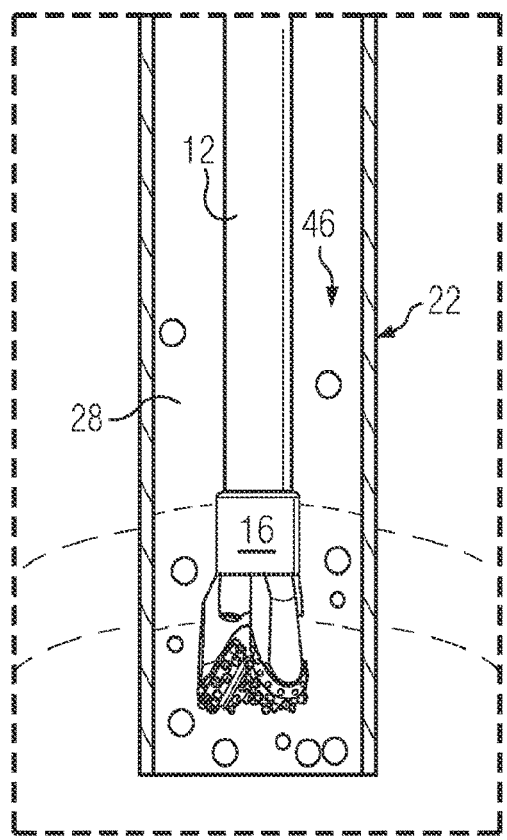
FIG. 3 depicts an example drill bit generating drill bit cuttings in use in the rig depicted on FIG. 1.

As further depicted on FIG. 1, drill bit cuttings that are formed by the drill bit 16 crushing rocks in the formation 24 may be removed from the returned drilling fluid 28 by a shale shaker 40 in the return flow line 34. The drilling fluid 28 may be reused and recirculated downhole. The shale shaker 40 may include a shaker pit 42 and a gas trap 44. FIG. 2 depicts drill bit cuttings 46 that have been removed from the drilling fluid 28 in the shaker pit 42 of the shale shaker 40 before the drilling fluid 28 is delivered to a mud pit 48. Moreover, FIG. 3 depicts cuttings flowing up through the borehole annulus after being generated by drill bit 16 during drilling.

As noted above, and depicted on FIG. 1, the rig 10 may include a system 50 configured to automatically evaluate cuttings images as described in greater detail herein. In certain example embodiments, the system may further include a digital camera configured to take digital images (such as calibrated digital images) of drill cuttings. The system 50 may further include computer hardware and software configured to automatically or semi-automatically evaluate cuttings images. To perform these functions, the hardware may include one or more processors (e.g., microprocessors) which may be connected to one or more data storage devices (e.g., hard drives or solid state memory to save the processed images). As is known to those of ordinary skill, the processors may be further connected to a network interface to enable communication with various surface and/or downhole sensors, gauges, and so forth as well as to communicate with actuators and other surface and/or downhole equipment. It will, of course, be understood that the disclosed embodiments are not limited the use of or the configuration of any particular computer hardware and/or software.

Turning now to FIG. 4, an example process 70 for obtaining cuttings images is depicted. A borehole is drilled at 72, for example, using the rig equipment described above with respect to FIG. 1. The drilling operation generates cuttings as also described above. The cuttings are collected at 74, for example, from a shale shaker 40, as described with respect to FIG. 2. In example embodiments the cuttings may be prepared for analysis at 76, for example, by drying in an oven and/or sieving or meshing the cuttings (e.g., as shown at 90) to remove large and/or small particles. The cuttings may further be placed on a tray 92 having a high contrast (vivid) background color to enhance particle identification and segmentation in the acquired images. The tray 92 may be placed in front of a camera 52 and a photo 94 may be taken at 78. In certain embodiments, the image acquisition process may make use of standardized and/or calibrated lighting, color enhancement, magnification, and/or focus/resolution settings. For example, in certain embodiments, color/illumination calibration is obtained by using colorimetry algorithms against previously analyzed photos 94 and a current photo of interest 94, while resolution calibration may be based on lens focal length, focal distance, and sensor size/resolution for the current photo 94 of interest as compared to that of previously analyzed photos 94. Images may be taken when the cuttings are wet or dry, with the humidity generally being controlled for dry cuttings images.

FIGS. 5A and 5B (collectively FIG. 5) depict flow charts of example methods 100 and 110 for segmenting a digital image to identify and label one or more lithology types in the image. In FIG. 5A, the cuttings image may be obtained at 102, for example, as described above with respect to FIG. 4. The received image may be processed with a trained NN, such as a trained CNN, at 104 to obtain a segmented image with at least one rock type label. The segmented image may include, for example, a pixel by pixel segmentation in which each pixel in the image is assigned a corresponding label (e.g., a lithology type or background label). The segmented image obtained at 104 and the acquired image obtained at 102 may be further processed at 106 to retrain the NN. For example, as described in more detail below, errors in the segmented image may be corrected (e.g., via relabeling the segmented image) and applied to the original image which may be in turn used to retrain the NN at 106. Another image (e.g., a subsequent image taken as drilling continues) may then be processed at 108 using the retrained NN to obtain a segmented image with at least one rock type.

In FIG. 5B, a cuttings image may be obtained at 102 and processed with a trained NN at 104 to obtain a segmented image with at least one rock type label (as described above with respect to FIG. 5A). Labeling errors may be identified and corrected in the segmented image at 116, thereby further assigning a corrected label (or labels) to certain pixels (or segments) in the acquired image. The identified errors may include, for example, mislabeled rocks in the segmented image (by mislabeled it may mean that certain ones of the rocks are labeled with an incorrect lithology type). The acquired (and relabeled) image may be divided (cropped) into a plurality of smaller images (crops) at 118. These individual crops may advantageously be significantly smaller than the original image. For example, the original image may be divided into a large number of crops, such as in a range from about 20 to about 400 crops per image (e.g., 32, 64, 96, 128, 160, 192, 256, or 320). A subset of the crops may be selected at 120 and added to a retraining database which is then used to retrain the NN at 122. In example embodiments, the subset of selected crops may include 10 percent or fewer of the number of crops in the image. Selecting a small number of crops may advantageously improve retraining time as described in more detail below. In certain example embodiments the NN retraining described above with respect to blocks 118, 120, and 122 may be executed when the errors identified at 116 exceed a predetermined threshold. In other embodiments, the NN may be retrained at some preselected interval (e.g., every second, fourth, eighth, or twelfth image). Another image (e.g., a subsequent image taken as drilling continues) may then be processed at 124 using the retrained NN to obtain a segmented image with at least one rock type label.

In FIG. 5, the acquired images are processed at 104 using a trained NN such as a trained CNN. The trained (or previously trained) NN may have been trained, for example, using a large number of annotated or labeled images, for example, of cuttings images including various lithology types from around the world or from the local basin (field or region). The training may result in weight optimization of the NN nodes and layers based on minimizing a loss function for the training dataset. In other words, the weights of each node in the multilayer NN may be tuned so that the model minimizes the errors when classifying the input images (or a subset thereof). It will be appreciated that the NN (e.g., CNN) generally includes multiple layers and that the initial training is intended to train each of the layers (e.g., each of the nodes in each of the layers is assigned a weight to minimize the loss function). The initial training may require large computing resources and may therefore be advantageously conducted offsite, for example, using an initial training database. This initial training often takes several hours (or longer) and is generally not repeated during the drilling operation.

With continued reference to FIG. 5, it will be appreciated that methods 100 and 110 disclose continuous learning methods in which the NN is continuously retrained during a drilling operation. By continuously retrained it is meant that segmentation errors are identified and corrected and then used to retrain the NN in substantially real time during the drilling operation or that the NN is retrained at some finite image interval while drilling. By real time it may be meant that the retraining is completed within a few minutes. Such continuous learning makes use of labeled (or relabeled) images acquired at earlier times or shallower depths in the drilling operation (e.g., at one or more of times t–1, t–2, . . . t–n or at one or more of depths d–1, d–2, . . . d–n). Thus, it will be understood that the NN may be retrained at 106 and 122 using one or more previously acquired images.

Figure 6:
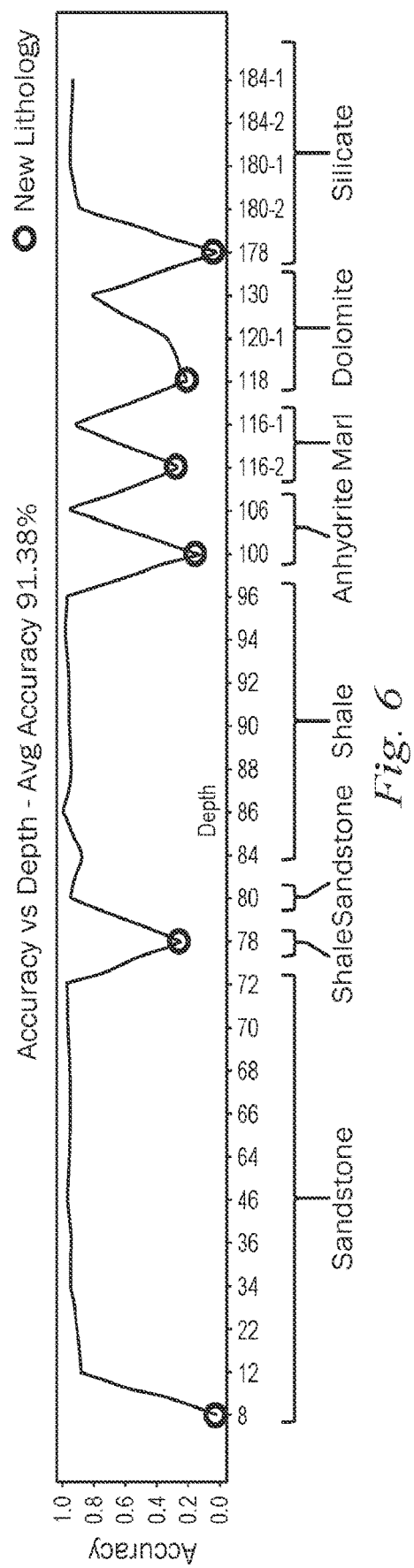
FIG. 6 depicts a plot of segmentation accuracy versus depth for an example operation.

In certain embodiments, it may be advantageous to retrain the NN when the segmentation accuracy falls below a predetermined threshold. FIG. 6 depicts a plot of segmentation accuracy in units of percentage versus depth (or a depth interval) for an example operation. The predominant lithology type is also labeled on the horizontal axis along with the depth interval. As depicted, the segmentation accuracy is generally very high (e.g., greater than 90 percent) with occasional dips in accuracy when a new lithology type is encountered. It has been found that identifying the lithology type of the cuttings is highly challenging. While NNs are known to be efficient at object recognition, they are also known to have limited or even non-existent generalization capacity on new classes. One aspect of the disclosed embodiments was the realization that regular (e.g., continuous as defined above) retraining of the NN may enable more efficient identification of new lithology types and a rapid improvement in accuracy with continued drilling. In FIG. 6, the red circles identify NN retraining upon encountering a new lithology. Note the rapid improvement in accuracy immediately following the retraining.

Another aspect of the disclosed embodiments was the realization that a retraining dataset needs to be balanced so as to enable the NN to learn from new lithology types and textures without forgetting what has been previously learned. For example only, the NN may be retrained so that it more efficiently recognizes shale without forgetting sandstone. This is illustrated at depths 70 through 90 on FIG. 6. The model was originally retrained at a depth of 8 to recognize sandstone and then continued to accurately identify sandstone cuttings at depths 12 through 72 (with accuracies approaching 100%). The accuracy dropped significantly as shale cuttings were encountered at a depth of 78. The NN was retrained to identify shale at a depth of 78. The accuracy increased significantly at a depth of 80 as the lithology temporality transitioned back to sandstone and then remained high at depths of 84 and above as the lithology again transitioned back to shale. By maintaining accuracy through these multiple transitions, the retrained NN demonstrated its ability to recognize a new lithology (shale) while maintaining memory of the earlier lithology (sandstone).

It will be appreciated that the retraining may involve fine tuning various NN model parameters, for example, including the learning rate, the weight given to various lithology classes, and the particular NN layers that may be retrained. Moreover, to enhance memory (or prevent memory loss), the retraining data may include images (or image crops) of older previously encountered lithology types. To further enhance memory and reduce training time, the retraining may advantageously only retrain a fraction of the NN layers, such as one half or fewer, one third or fewer, or one quarter or fewer of the NN layers. The retrained layers may further advantageously be the last NN layers. In certain embodiments, the retraining may only retrain a few of the NN layers, such as the last three or fewer (e.g., 1, 2, or 3) NN layers. For example, by only retraining a selected subset of the NN layers, the retraining time may be reduced to a few minutes, yet significantly improve accuracy.

With continued reference to FIG. 5B, the retraining image(s) may be advantageously divided into a set of crops (small pieces or portions of the original image). A smaller subset of the crops may be manually or automatically selected to retrain the model. The use of a relatively small subset of the crops may advantageously reduce the retraining time, which may be critical to use of the method 110 in substantially real time while drilling. It will be understood that it would be impractical (and extremely expensive) for a drilling operator to wait for a NN to be retrained so that subsequent images may be segmented. To improve retraining accuracy and convergence speed, the crops may be further weighted, shuffled, augmented, transformed (e.g., rotated or flipped), color shifted, and may include sections that are erased. Such crop processing may be important in certain operations, for example, to reduce overfitting.

Turning now to FIGS. 7A-7E (collectively FIG. 7) the disclosed embodiments are described in further detail by way of a hypothetical example. As described above, a trained CNN is received or prepared for the drilling operation. In this particular example, the wellbore was initially drilled through a shale formation and the initial retraining database included only shale crops as depicted on FIG. 7A. The trained NN was used to process an acquired image as depicted on FIG. 7B. At this particular depth, the formation had changed from shale to primarily sandstone. This resulted in significant labeling errors as indicated since the NN had been retrained and optimized for shale using the retraining database shown on FIG. 7A. The segmented image may be relabeled, for example, manually using a software application as shown on FIG. 7C.

Figure 7A:
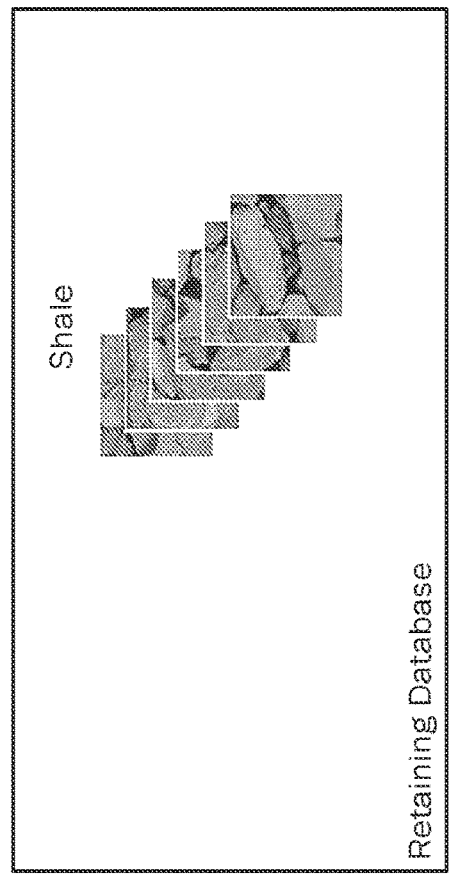
FIGS. 7A, 7B, 7C, 7D, and 7E (collectively FIG. 7) depicts a hypothetical example that further illustrates the disclosed method.
Figure 7B:
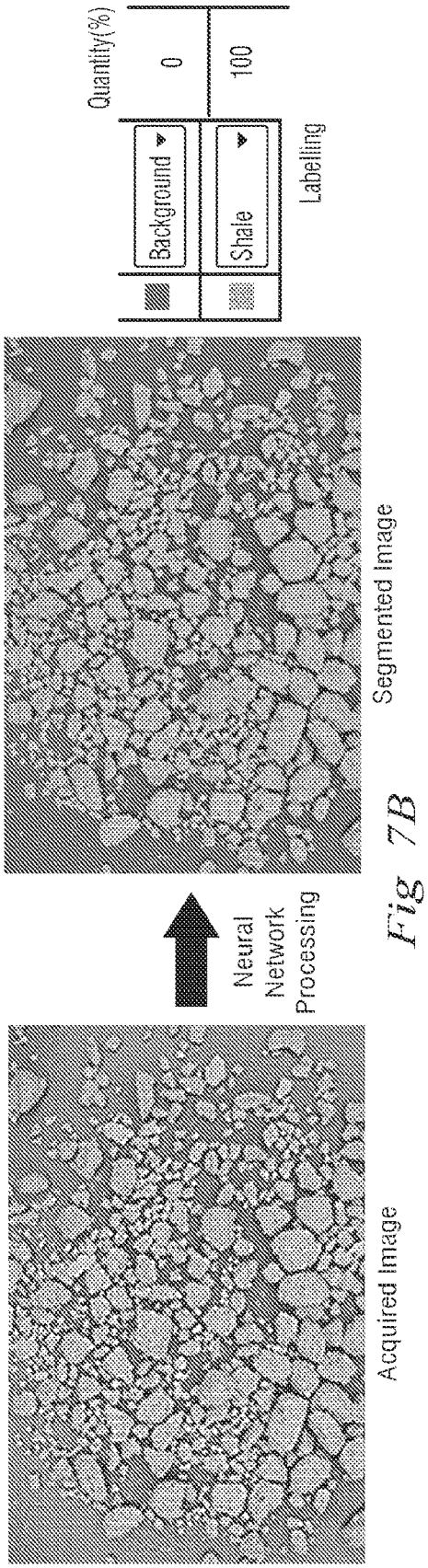
Figure 7C:
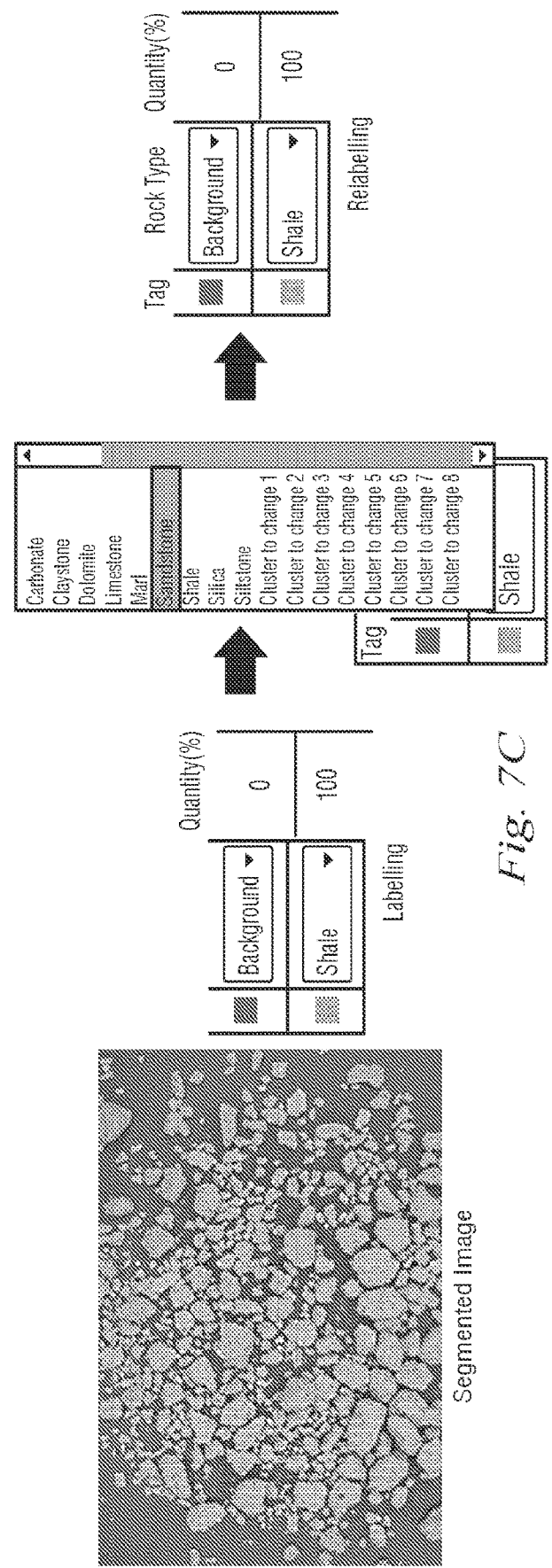
Figure 7D:
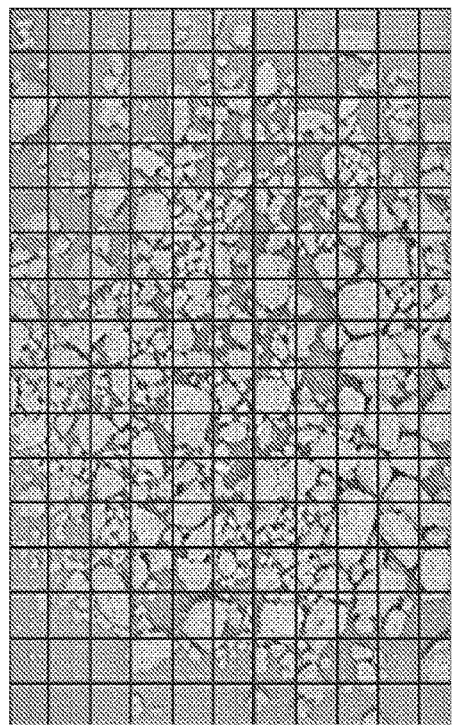
Figure 7D:
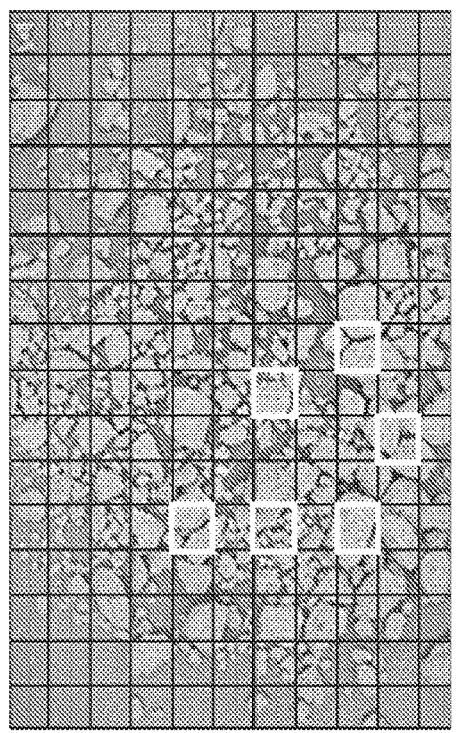

FIG. 7D depicts an example cropped image. A subset of the crops may be selected manually or via a smart selection algorithm as depicted. The algorithm may be advantageously configured to select only those crops having the most information regarding the depicted lithology types (e.g., information related to shape, color, texture, number of individual rocks, etc.). In one example embodiment, the algorithm is configured to select the crops that maximize entropy so as to generate an exhaustive and heterogeneous dataset. This may be accomplished, for example, by extracting a listing of features for each crop using the NN. A clustering algorithm may then be used to cluster the crops using the extracted list of features and remove duplicate crops (crops that are similar to one another) or crops that are too far (greater than a threshold distance) from the centroid of each cluster.

Figure 7E:
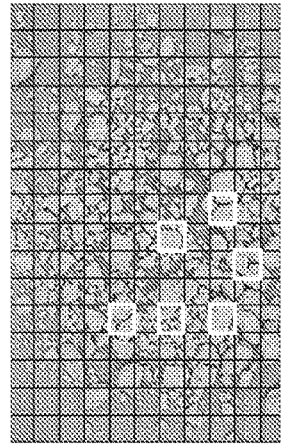
Figure 7E:
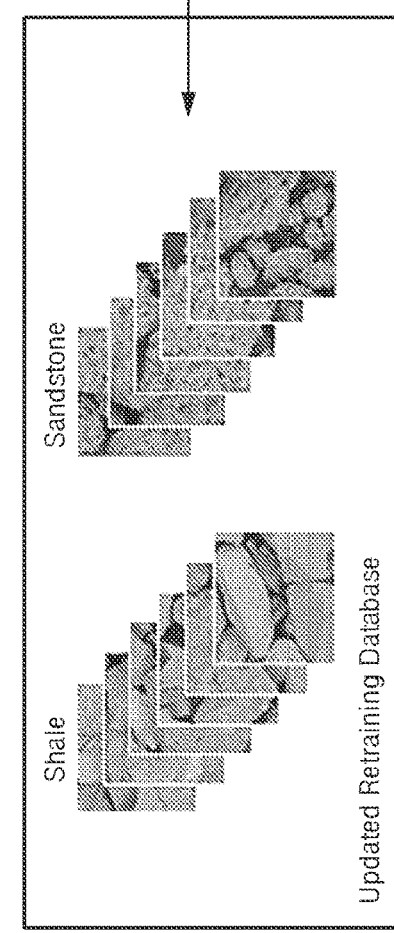
Figure 7E:
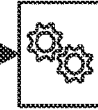

The selected crops may then be added to the retraining database as depicted on FIG. 7E. The crops in the retraining database may then be optionally further processed, for example, using the above described algorithm to further select the most important crops for retraining. Note that the retraining database now includes both shale and sandstone crops (to improve accuracy and to retain memory). Moreover, each crop may be assigned a weight. For example, an increasing weight may increase the likelihood that a particular crop is selected. In one example embodiment, the more recently an image has been labeled in the well, the higher weight it is given, thereby increasing the likelihood of selection. From a geological standpoint, it will be appreciated that it is more likely that a rock taken at a depth of 500 meters is more similar to a rock taken at a depth of 490 meters, than one at 10 meters. As further depicted (and described above), the retraining database is used to retrain preselected layers of the NN. The retrained NN may then be used to process the next cuttings image. It will be understood that the above described retraining process may be repeated at substantially any suitable number of times while drilling. The retraining database may include crops with numerous lithology types depending on the particular formation structure of the basin.

It will be understood that the present disclosure includes numerous embodiments. These embodiments include, but are not limited to, the following embodiments.

In a first embodiment, a method for evaluating drill cuttings obtained during a wellbore drilling operation includes acquiring a first digital image of drill cuttings obtained during the wellbore drilling operation; evaluating the first digital image with a trained neural network (NN) to generate a first segmented image including a plurality of labels in which at least one label includes a lithology type; correcting labeling errors in the first segmented image and using a portion of the corrected first segmented image to retrain the NN; acquiring a second digital image of drill cuttings obtained during the wellbore drilling operation; and evaluating the second digital image with the retrained NN to generate a second segmented image including a plurality of labels in which at least one label includes a lithology type.

A second embodiment may include the first embodiment, wherein the acquiring the first digital image and the acquiring the second digital image comprises drilling a subterranean wellbore; collecting first drill cuttings and second drill cuttings from circulating drilling fluid used while drilling the subterranean wellbore; preparing the first drill cuttings and the second drill cuttings; and taking a first digital photograph of the prepared first drill cuttings and a second digital photograph of the prepared second drill cuttings.

A third embodiment may include the second embodiment, wherein the first drill cuttings are generated at a first depth in the wellbore and the second drill cuttings are generated at a second depth in the wellbore, the second depth being greater than the first depth.

A fourth embodiment may include any one of the first through third embodiments, wherein the correcting the labeling errors comprises identifying and correcting labeling errors in the first segmented image to obtain a corrected image; dividing the corrected image into a plurality of crops; selecting a subset of the plurality of crops and adding the selected subset to a retraining database; and retraining the NN using the retraining database.

A fifth embodiment may include the fourth embodiment, wherein the subset of the plurality of crops is selected to include drill cuttings having a lithology type that was mislabeled in the first segmented image.

A sixth embodiment may include any one of the fourth through fifth embodiments, wherein the plurality of crops comprises from 20 to 400 crops; and the subset includes 10 percent or fewer of the crops of the plurality of crops.

A seventh embodiment may include any one of the fourth through sixth embodiments, wherein the selecting the subset of the plurality of crops is performed automatically to maximize entropy.

An eighth embodiment may include the seventh embodiment, wherein the selecting the subset of the plurality of crops comprises extracting a listing of features for each of the plurality of crops using the NN; clustering the plurality of crops using the extracted list of features; and removing duplicate ones of the clustered crops or crops that exceed a threshold distance from a centroid of each cluster in the clustering to select the subset.

A ninth embodiment may include any one of the first through eighth embodiments, wherein the NN network includes a plurality of layers and the retraining the NN retrains half or fewer of the plurality of layers.

A tenth embodiment may include the ninth embodiment wherein the retraining the NN retrains only the last three or fewer layers of the NN.

In an eleventh embodiment, a system for evaluating drill cuttings obtained during a wellbore drilling operation comprises a digital camera configured to take digital images of drill cuttings; and a computer processor configured to cause the digital camera to acquire a first digital image of drill cuttings obtained during the wellbore drilling operation; evaluate the first digital image with a trained neural network (NN) to generate a first segmented image including a plurality of labels in which at least one label includes a lithology type; retrain the NN using a portion of the first segmented image that includes corrected labeling errors; cause the digital camera to acquire a second digital image of drill cuttings obtained during the wellbore drilling operation; and evaluate the second digital image with the retrained NN to generate a second segmented image including a plurality of labels in which at least one label includes a lithology type.

A twelfth embodiment may include the eleventh embodiment, wherein the retrain the NN comprises divide the first segmented image into a plurality of crops; select a subset of the plurality of crops and add the selected subset to a retraining database; and retrain the NN using the retraining database.

A thirteenth embodiment may include the twelfth embodiment, wherein the plurality of crops comprises from 20 to 400 crops; and the subset includes 10 percent or fewer of the crops of the plurality of crops.

A fourteenth embodiment may include any one of the twelfth through thirteenth embodiments, wherein the select the subset of the plurality of crops is performed automatically to maximize entropy and comprises extract a listing of features for each of the plurality of crops using the NN; cluster the plurality of crops using the extracted list of features; and remove duplicate ones of the clustered crops or crops that exceed a threshold distance from a centroid of each cluster in the clustering to selected the subset.

A fifteenth embodiment may include any one of the eleventh through fourteenth embodiments, wherein the NN network includes a plurality of layers and the retrain the NN retrains half or fewer of the plurality of layers or only retrains the last three or fewer layers of the NN.

In a sixteenth embodiment, a method for evaluating drill cuttings obtained during a wellbore drilling operation comprises acquiring a first digital image of drill cuttings obtained during the wellbore drilling operation; evaluating the first cuttings image with a trained neural network (NN) to generate a first segmented image including a plurality of labels in which at least one label includes a lithology type; identifying and correcting labeling errors in the first segmented image; dividing the corrected first segmented image into a plurality of crops; selecting a subset of the plurality of crops and adding the selected subset to a retraining database; retraining the NN using the retraining database; acquiring a second digital image of drill cuttings obtained during the wellbore drilling operation; and evaluating the second digital image with the retrained NN to generate a second segmented image including a plurality of labels in which at least one label includes a lithology type.

A seventeenth embodiment may include the sixteenth embodiment, wherein the acquiring the first digital image and the acquiring the second digital image comprises drilling a subterranean wellbore; collecting first drill cuttings and second drill cuttings from circulating drilling fluid used while drilling the subterranean wellbore; preparing the first drill cuttings and the second drill cuttings; and taking a first digital photograph of the prepared first drill cuttings and a second digital photograph of the prepared second drill cuttings.

An eighteenth embodiment may include any one of the sixteenth through seventeenth embodiments, wherein the crops are selected to include a lithology type that was mislabeled in the first segmented image; the plurality of crops comprises from 20 to 400 crops; and the subset includes 10 percent or fewer of the crops of the plurality of crops.

A nineteenth embodiment may include any one of the sixteenth through eighteenth embodiments, wherein the selecting the subset of the plurality of crops is performed automatically to maximize entropy and comprises extracting a listing of features for each of the plurality of crops using the NN; clustering the plurality of crops using the extracted list of features; and removing duplicate ones of the clustered crops or crops that exceed a threshold distance from a centroid of each cluster in the clustering to selected the subset.

A twentieth embodiment may include any one of the sixteenth through nineteenth embodiments, wherein the NN network includes a plurality of layers and the retraining the NN retrains half or fewer of the plurality of layers or only retrains the last three or fewer layers of the NN.

Although automated image-based rock type identification with neural-network segmentation and continuous learning has been described in detail, it should be understood that various changes, substitutions and alternations can be made herein without departing from the spirit and scope of the disclosure as defined by the appended claims.

The invention claimed is:

1. A method for evaluating drill cuttings obtained during a wellbore drilling operation, the method comprising:
acquiring a first digital image of first drill cuttings obtained during the wellbore drilling operation;
evaluating the first digital image with a trained neural network (NN) to generate a first segmented image including a plurality of labels in which at least one label includes a lithology type;
correcting labeling errors in the first segmented image and using a portion of the corrected first segmented image to retrain the NN, wherein the correcting the labeling errors comprises:
identifying and correcting labeling errors in the first segmented image to obtain a corrected image;
dividing the corrected image into a plurality of crops;
selecting a subset of the plurality of crops and adding the selected subset to a retraining database; and
retraining the NN using the retraining database;
acquiring a second digital image of second drill cuttings obtained during the wellbore drilling operation; and
evaluating the second digital image with the retrained NN to generate a second segmented image including a plurality of labels in which at least one label includes a lithology type.

2. The method of claim 1, wherein the acquiring the first digital image and the acquiring the second digital image comprises:
drilling a subterranean wellbore;
collecting the first drill cuttings and the second drill cuttings from circulating drilling fluid used while drilling the subterranean wellbore;
preparing the first drill cuttings and the second drill cuttings; and
taking a first digital photograph of the prepared first drill cuttings and a second digital photograph of the prepared second drill cuttings.

3. The method of claim 2, wherein the first drill cuttings are generated at a first depth in the wellbore and the second drill cuttings are generated at a second depth in the wellbore, the second depth being greater than the first depth.

4. The method of claim 1, wherein the subset of the plurality of crops is selected to include drill cuttings having a lithology type that was mislabeled in the first segmented image.

5. The method of claim 1, wherein:
the plurality of crops comprises from 20 to 400 crops; and
the subset includes 10 percent or fewer of the crops of the plurality of crops.

6. The method of claim 1, wherein the selecting the subset of the plurality of crops is performed automatically to maximize entropy.

7. The method of claim 6, wherein the selecting the subset of the plurality of crops comprises:
extracting a listing of features for each of the plurality of crops using the NN;
clustering the plurality of crops using the extracted list of features; and
removing duplicate ones of the clustered crops or crops that exceed a threshold distance from a centroid of each cluster in the clustering to select the subset.

8. The method of claim 1, wherein the NN network includes a plurality of layers and the retraining the NN retrains half or fewer of the plurality of layers.

9. The method of claim 8, wherein the retraining the NN retrains only the last three or fewer layers of the NN.

10. A system for evaluating drill cuttings obtained during a wellbore drilling operation, the system comprising:
a digital camera configured to take digital images of drill cuttings; and
a computer processor configured to:
cause the digital camera to acquire a first digital image of first drill cuttings obtained during the wellbore drilling operation;
evaluate the first digital image with a trained neural network (NN) to generate a first segmented image including a plurality of labels in which at least one label includes a lithology type;
retrain the NN using a portion of the first segmented image that includes corrected labeling errors, wherein the retrain the NN comprises:
divide the first segmented image into a plurality of crops;
select a subset of the plurality of crops and add the selected subset to a retraining database; and
retrain the NN using the retraining database;
cause the digital camera to acquire a second digital image of second drill cuttings obtained during the wellbore drilling operation; and
evaluate the second digital image with the retrained NN to generate a second segmented image including a plurality of labels in which at least one label includes a lithology type.

11. The system of claim 10, wherein:
the plurality of crops comprises from 20 to 400 crops; and
the subset includes 10 percent or fewer of the crops of the plurality of crops.

12. The system of claim 10, wherein the select the subset of the plurality of crops is performed automatically to maximize entropy and comprises:
extract a listing of features for each of the plurality of crops using the NN;
cluster the plurality of crops using the extracted list of features; and
remove duplicate ones of the clustered crops or crops that exceed a threshold distance from a centroid of each cluster in the clustering to selected the subset.

13. The system of claim 10, wherein the NN network includes a plurality of layers and the retrain the NN retrains half or fewer of the plurality of layers or only retrains the last three or fewer layers of the NN.

14. A method for evaluating drill cuttings obtained during a wellbore drilling operation, the method comprising:
acquiring a first digital image of first drill cuttings obtained during the wellbore drilling operation;
evaluating the first digital image with a trained neural network (NN) to generate a first segmented image including a plurality of labels in which at least one label includes a lithology type;
identifying and correcting labeling errors in the first segmented image;
dividing the corrected first segmented image into a plurality of crops;
selecting a subset of the plurality of crops and adding the selected subset to a retraining database;
retraining the NN using the retraining database;
acquiring a second digital image of second drill cuttings obtained during the wellbore drilling operation; and
evaluating the second digital image with the retrained NN to generate a second segmented image including a plurality of labels in which at least one label includes a lithology type.

15. The method of claim 14, wherein the acquiring the first digital image and the acquiring the second digital image comprises:
drilling a subterranean wellbore;
collecting the first drill cuttings and the second drill cuttings from circulating drilling fluid used while drilling the subterranean wellbore;
preparing the first drill cuttings and the second drill cuttings; and
taking a first digital photograph of the prepared first drill cuttings and a second digital photograph of the prepared second drill cuttings.

16. The method of claim 14, wherein:
the crops are selected to include a lithology type that was mislabeled in the first segmented image;
the plurality of crops comprises from 20 to 400 crops; and
the subset includes 10 percent or fewer of the crops of the plurality of crops.

17. The method of claim 14, wherein the selecting the subset of the plurality of crops is performed automatically to maximize entropy and comprises:
extracting a listing of features for each of the plurality of crops using the NN;
clustering the plurality of crops using the extracted list of features; and
removing duplicate ones of the clustered crops or crops that exceed a threshold distance from a centroid of each cluster in the clustering to selected the subset.

18. The method of claim 14, wherein the NN network includes a plurality of layers and the retraining the NN retrains half or fewer of the plurality of layers or only retrains the last three or fewer layers of the NN.

* * * * *